(12) United States Patent
Frank

(10) Patent No.: US 8,183,032 B2
(45) Date of Patent: May 22, 2012

(54) SEMI-CLOSED LOOP ALGA-DIESEL FUEL PHOTOBIOREACTOR USING WASTE WATER

(75) Inventor: David L. Frank, Highland Beach, FL (US)

(73) Assignee: Innovative American Technology Inc., Coconut Creek, FL (US)

( * ) Notice: Subject to any disclaimer, the term of this patent is extended or adjusted under 35 U.S.C. 154(b) by 447 days.

(21) Appl. No.: 12/549,656

(22) Filed: Aug. 28, 2009

(65) Prior Publication Data

US 2010/0055765 A1    Mar. 4, 2010

Related U.S. Application Data

(60) Provisional application No. 61/190,399, filed on Aug. 28, 2008.

(51) Int. Cl.
*C12M 3/02* (2006.01)
*C12N 1/12* (2006.01)

(52) U.S. Cl. .................. 435/257.1; 435/292.1

(58) Field of Classification Search .............. 435/257.1, 435/292.1
See application file for complete search history.

(56) References Cited

U.S. PATENT DOCUMENTS

| | | | |
|---|---|---|---|
| 4,158,773 A | 6/1979 | Novak | |
| 4,799,828 A | 1/1989 | Georgii | |
| 5,056,958 A | 10/1991 | Campbell | |
| 5,104,803 A | 4/1992 | Delente | |
| 5,137,828 A | 8/1992 | Robinson et al. | |
| 5,241,573 A | 8/1993 | Thacker | |
| 5,242,827 A | 9/1993 | Chaumont et al. | |
| 5,614,378 A | 3/1997 | Yang et al. | |
| 5,633,508 A | 5/1997 | Schleppenbach | |
| 5,665,970 A | 9/1997 | Kronenberg et al. | |
| 5,838,759 A | 11/1998 | Armistead | |
| 6,174,720 B1 | 1/2001 | Oxley et al. | |
| 6,370,222 B1 | 4/2002 | Cornick | |
| 6,433,335 B1 | 8/2002 | Kronenberg et al. | |
| 6,479,826 B1 | 11/2002 | Klann et al. | |
| 6,545,281 B1 | 4/2003 | McGregor et al. | |
| 6,845,873 B1 | 1/2005 | Chattey | |
| 6,891,470 B2 | 5/2005 | Bohinc | |
| 6,937,692 B2 | 8/2005 | Johnson | |
| 6,980,483 B2 | 12/2005 | McDonald | |
| 6,998,617 B2 | 2/2006 | D'Emilio et al. | |
| 7,026,944 B2 | 4/2006 | Alioto et al. | |
| 7,030,755 B2 | 4/2006 | Bohinc | |
| 7,064,336 B2 | 6/2006 | Archer et al. | |
| 7,116,235 B2 | 10/2006 | Alioto et al. | |
| 7,151,447 B1 | 12/2006 | Willms et al. | |
| 7,183,554 B2 | 2/2007 | Gallagher et al. | |
| 7,356,115 B2 | 4/2008 | Ford et al. | |
| 2002/0175291 A1 | 11/2002 | Reeder et al. | |
| 2003/0108150 A1 | 6/2003 | Franke | |
| 2003/0144800 A1 | 7/2003 | Davis et al. | |
| 2003/0165211 A1 | 9/2003 | Grodzins et al. | |
| 2003/0201394 A1 | 10/2003 | Peoples | |
| 2004/0018060 A1 | 1/2004 | Knezek et al. | |
| 2004/0119591 A1 | 6/2004 | Peeters | |
| 2004/0126895 A1 | 7/2004 | Overbeck et al. | |
| 2004/0148137 A1 | 7/2004 | Zerwekh et al. | |
| 2005/0011849 A1 | 1/2005 | Chattey | |
| 2005/0023477 A1 | 2/2005 | Archer et al. | |
| 2005/0082485 A1 | 4/2005 | Torii | |
| 2005/0156734 A1 | 7/2005 | Zerwekh et al. | |
| 2005/0205793 A1 | 9/2005 | Bohinc | |
| 2005/0220247 A1 | 10/2005 | Ruddy et al. | |
| 2005/0258372 A1 | 11/2005 | McGregor et al. | |
| 2005/0275545 A1 | 12/2005 | Alioto et al. | |
| 2006/0097171 A1 | 5/2006 | Balchunas et al. | |
| 2006/0138331 A1 | 6/2006 | Guillebaud et al. | |
| 2006/0141615 A1 | 6/2006 | Lu | |
| 2006/0284094 A1 | 12/2006 | Inbar | |
| 2007/0001123 A1 | 1/2007 | Andrews et al. | |

FOREIGN PATENT DOCUMENTS

| | | |
|---|---|---|
| JP | 56-76540 A | 6/1981 |
| KR | 10-1992-7004134 | 12/1992 |
| KR | 10-1005-0067392 | 7/2005 |
| WO | WO 94/09112 A1 | 4/1994 |
| WO | WO98-00681 | 1/1998 |
| WO | WO2006-085999 | 8/2006 |

OTHER PUBLICATIONS

U.S. Appl. No. 11/291,574, filed Dec. 2005, Frank.
U.S. Appl. No. 11/363,594, filed Feb. 2006, Frank.
U.S. Appl. No. 11/564,193, filed Nov. 2006, Frank.
U.S. Appl. No. 11/931,370, filed Oct. 2007, Frank.
International Preliminary Report on Patentabiilty for PCT/US06/46255 mailed Sep. 24, 2008.

(Continued)

*Primary Examiner* — Herbert J Lilling
(74) *Attorney, Agent, or Firm* — Jose Gutman; Fleit Gibbons Gutman Bongini & Bianco PL

(57) ABSTRACT

A semi-closed loop diesel photobioreactor system and method are provided for producing diesel fuel from wild algae or from specialized algae that has been biologically modified for high efficiency oil production using waste water as a primary food source. The diesel photobioreactor provides a semi-closed loop system with an opening to acquire waste water below the surface to obtain waste water nutrients and to protect the algae species from contamination. The semi-closed loop diesel photobioreactor includes a container that can be designed in a variety of shapes with a tube design preferred, and containing a liquid culture medium for cultivating photosynthetic organisms. The system can utilize natural light and can also deploy an innovative lighting system integrated into the photobioreactor container. The diesel photobioreactor system also has one or more cleaning devices mounted within the container for cleaning the surface of the photobioreactor container.

19 Claims, 5 Drawing Sheets

OTHER PUBLICATIONS

International Search Report and Written Opinion of the International Searching Authority for PCT/US06/46255 mailed Sep. 25, 2007.
Written Opinion of the International Searching Authority for PCT/US07/085578 dated Jan. 23, 2009.
International Search Report for PCT/US07/085578 dated Jan. 23, 2009.
PCT Application No. PCT/US2007/085578 filed Nov. 27, 2007.
PCT Application No. PCT/US2006/46255 filed Nov. 30, 2006.
Non-Final Rejection for U.S. Appl. No. 11/291,574 dated Dec. 2, 2008.
Final Rejection for U.S. Appl. No. 11/291,574 dated Mar. 20, 2008.
Notice of Allowance for U.S. Appl. No. 11/291,574 dated May 20, 2009.
Non-Final Rejection for U.S. Appl. No. 11/363,594 dated Aug. 23, 2006.
Notice of Allowance for U.S. Appl. No. 11/363,594 dated Sep. 27, 2006.
Non-Final Rejection for U.S. Appl. No. 11/564,183 dated Jun. 25, 2009.
Non-Final Rejection for U.S. Appl. No. 11/931,370 dated Dec. 12, 2008.
Final Rejection for U.S. Appl. No. 11/931,370 dated Sep. 9, 2009.
Final Rejection for U.S. Appl. No. 11/564,193 dated Jan. 8, 2010.
Notice of Allowance for U.S. Appl. No. 11/930,229 dated Apr. 7, 2010.
International Search Report and Written Opinion for PCT/US09/050299 dated Mar. 3, 2010.
Notice of Allowance for U.S. Appl. No. 11/931,370 dated Mar. 30, 2010.
International Search Report for PCT/US09/038064 dated Jul. 31, 2009.
International Search Report and Written Opinion for PCT/US09/044486 dated Dec. 23, 2009.
International Search Report and Written Opinion for PCT/US09/044475 dated Jan. 6, 2010.
International Search Report and Written Opinion for PCT/US09/045268 dated Jan. 29, 2010.
International Search Report and Written Opinion for PCT/US09/044494 dated Jan. 18, 2010.
Non-Final Rejection for U.S. Appl. No. 11/931,211 dated Apr. 30, 2010.
Travieso, L., et al., "A Helical Tubular Photobioreactor Producing Spirulina in a Semicontinuous Mode", Int'l Biodeterioration & Biodegradation, 2001, vol. 47, pp. 151-155.
Pulz, Otto, et al., "Photobioreactors: Design and Performance with Respect to Light Energy Input", Advances in Biochemical Engineering/Biotechnology, 1998, vol. 59, pp. 123-152.
Scragg, A.H., et al., "Growth of Microalgae with Increased Caloric Values in a Tubular Bioreactor", Biomass and Bioenergy, 2002, vol. 23, pp. 67-73.
Molina, E., "Tubular Photobioreactor Design for Algal Cultures", J. of Biotechnology, 2001, vol. 92, pp. 113-131.
International Search Report and Written Opinion for PCT/US09/055333 dated Mar. 16, 2010.

SEMI-CLOSED LOOP ALGA-DIESEL FUEL PHOTOBIOREACTOR USING WASTE WATER

CROSS-REFERENCE TO RELATED APPLICATION

This application is based upon and claims priority from prior provisional patent application No. 61/190,399, filed on Aug. 28, 2008, entitled "Semi-Closed Loop Alga-Diesel Fuel Photobioreactor Using Waste Water", the entire teachings thereof being herein incorporated by reference.

FIELD OF THE INVENTION

The present invention generally relates to the field of algae fuel bioreactors, and more particularly relates to an alga-diesel fuel photobioreactor using waste water.

BACKGROUND OF THE INVENTION

Production of algae oils for refinement to create diesel fuels has been produced in open ponds using waste water as a food for the algae. Various approaches of algae production are known in the art. Photobioreactors have been described using shallow lagoons agitated with one or several paddle wheels. The photobioreactors of this first generation have the disadvantage of offering poor productivity to the seasonal and daily climatic variations and are thus to be confined to tropical and subtropical areas. They also have the disadvantage of being prone to a variety of contaminations including other algae species.

Other approaches to algae production have emerged over the past years. An example is the use of closed cultivating systems which have gained popularity because they address most of the limitations of the conventional shallow lagoon designs. The most popular closed cultivating systems are the tubular photobioreactors whose configuration allows high production rates due to the optimization of their light path, their temperature control and their culture mixture. This second generation of photobioreactors allows for an automated control and a more effective management. It also allows the pH of the culture medium to be lowered. Examples of tubular photobioreactors are shown in U.S. Pat. Nos. 5,137,828; 5,242,827 and 6,174,720. These closed loop systems require many supplements to be added to provide nutrients for algae growth.

Artificial light has been applied as an energy source for the growth of microalgae in Photobioreactors of various shapes. Examples of these photobioreactors are provided in U.S. Pat. Nos. 5,104,803 and 5,614,378. Adhesions of microalgae occur in a natural manner, particularly on the walls where light is emitted. The effect of adhesion of microalgae on the photobioreactor wall causes a reduction in the culture exposed to the light and raises the risks of contamination.

Although many photobioreactors have been proposed in the prior art, and there have been attempts to create diesel fuel using algae feeding on waste water, there is still a need for an improved diesel photobioreactor that enables volume production efficiencies at a cost effective basis for a commercial application.

Therefore, a need exists to overcome the problems with the prior art as discussed above.

SUMMARY OF THE INVENTION

According to various embodiments of the present invention, a semi-closed loop diesel photobioreactor system is used to produce diesel fuel from wild algae, or from specialized algae that has been biologically modified for high efficiency oil production, using waste water as a primary food source. The diesel photobioreactor system provides a semi-closed loop system with an opening to acquire waste water below the surface to obtain waste water nutrients and to protect the algae species from contamination. A semi-closed loop diesel photobioreactor container can be designed in a variety of shapes with a tube design as the preferred embodiment for containing a liquid culture medium for cultivating photosynthetic organisms. The system can utilize natural light and can also deploy an innovative lighting system integrated into the bioreactor tube. The diesel photobioreactor container also has cleaning devices mounted within the container for cleaning the surface of the photobioreactor tube.

According to one embodiment, a semi-closed loop system for algae production of diesel oil using waste water as the primary nutrient and the byproducts of this process is offered to address the issues described above. The semi-closed loop system draws waste water into the photobioreactor tube to supply nutrients supporting the algae culture. The semi-closed loop photobioreactor is designed as a controlled environment to enable high efficiency algae production. The semi-closed loop photobioreactor container is designed with an integrated lighting system that reduces microalgae adhesion. The semi-closed loop photobioreactor system, for example, uses a brush system pushed or pulled through the photobioreactor container tube to clean the inside of the photobioreactor tube. For examples see FIGS. 7 and 8. As illustrated in FIG. 7, a cleaning device can be moved through the photobioreactor tube 702 by water propulsion (indicated by the arrows 704) through the tube, thereby cleaning the inner sides of the tube 702 as the device passes through the tube. One example of such cleaning device comprises one or more brushes 706 that are pushed through the tube 702 by water propulsion 704. A second example of the device comprises a cleaning solvent or microbes (either or both represented by 708) that may be used to clean the inner surface of the photobioreactor tube 702. Additionally, a cleaning device 804 can be pushed-pulled through the photobioreactor tube 802 by magnetic propulsion 807, thereby cleaning the inner side of the tube 802 as the cleaning device 804 passes through the tube 802. For example, a cleaning brush device 804 includes a magnet 805 inserted inside the cleaning device 804. A second magnet 806 is moved 810 along the outside of the photobioreactor tube 802. Magnetic propulsion 807 causes the cleaning brush device 804 inside the tube 802 to move 812 according to the movement 810 of the second magnet 806 outside of the photobioreactor tube 802. The cleaning brush device 804 deployed inside the tube is drawn through the tube 802 by the second magnet passing along the outside of the tube, thereby cleaning the inner sides of the tube as the cleaning brush device 804 passes through the tube 802. The example of a cleaning brush device 804 is not limiting. It is only one example of many different types of cleaning devices 804 that can be moved inside the tube 802. Additionally, while the examples of propulsion illustrated above include water propulsion and magnetic propulsion. These are non-limiting examples of many different types of propulsion that move cleaning devices 706, 708, 804, inside the bioreactor tube 702, 802. For example, one or more guide wires, or similar mechanism, can be attached to the cleaning device 706 inside the tube 702. The guide wires pull (either forward or backward) the cleaning device 706 through the tube 702 thereby moving the cleaning device 706 (which in one example includes one or more brushes) to clean the inner side of the tube 702.

The semi-closed loop photobioreactor system provides greater efficiency and productivity, for either wild and/or biologically modified algae species over open pond system through management and control of the environment, optional use of assisted artificial light as an energy source for photosynthesis and the deployment of an automated cleaning process for the photobioreactor tube.

The semi-closed loop system can be a closed loop photobioreactor with a pipe extended into a waste water holding area to draw waste water and materials into the photobioreactor.

Sewage treatment or domestic wastewater treatment facilities perform the process of removing contaminants from wastewater, both runoff (effluents) and domestic. It includes physical, chemical and biological processes to remove physical, chemical, and biological contaminants. Its objective is to produce a waste stream (or treated effluent) and a solid waste or sludge suitable for discharge or reuse back into the environment. The semi-closed loop photobioreactor system uses the waste water effluent at multiple stages of treatment as nutrients for the production of diesel fuel from algae.

Typical micro nutrients used in algae growth are: Ca, Cu, Fe, Mg, Mn, Mo, K, and Zn.

A concentrated nutrient source can be created by subjecting the waste water effluent to very high pressure prior to introducing the waste water to the photobioreactor. This process increases exchange between the nutrients and the algae culture.

According to one embodiment, an integrated lighting system using light tubes supports high efficiency algae production environment. The integrated lighting system, according to one embodiment, is deployed within the photobioreactor tube and is constructed of materials that greatly reduce or eliminate micro-algae adhesion to the lighting system. The deployment of the lighting system within the photobioreactor tube greatly reduces or eliminates the area on the photobioreactor tube that micro-algae would naturally adhere to.

Transparent hollow light tubes, in contrast to an optical fiber which has a solid core, include a prism light guide that directs light through air and is therefore referred to as hollow light guide. The light tubes, according to one embodiment, are integrated into the sides of the photobioreactor tubes.

A scrub brush, according to one embodiment, is deployed within the photobioreactor tube and is pushed or pulled through the tube to clean the inside of the photobioreactor tube and lighting system.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

As required, detailed embodiments of the present invention are disclosed herein; however, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure and function. Further, the terms and phrases used herein are not intended to be limiting; but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

A semi-closed loop diesel photobioreactor and production method of diesel fuel from wild algae or from specialized algae that has been biologically modified for high efficiency oil production using waste water as a primary food source is disclosed. The diesel photobioreactor provides a semi closed loop system with an opening to acquire waste water below the surface to obtain waste water nutrients and to protect the algae species from contamination. The semi-closed loop diesel photobioreactor can be designed in a variety of shapes with a tube design as the preferred embodiment containing a liquid culture medium for cultivating photosynthetic organisms. The system can utilize natural light and can also deploy an innovative lighting system integrated into the bioreactor tube. The diesel photobioreactor also has cleaning devices mounted within the container for cleaning the surface of the photobioreactor tube.

The semi-closed loop system is described as a closed loop photobioreactor with a pipe extended into a waste water holding area to draw waste water and materials into the photobioreactor.

Figure 6:
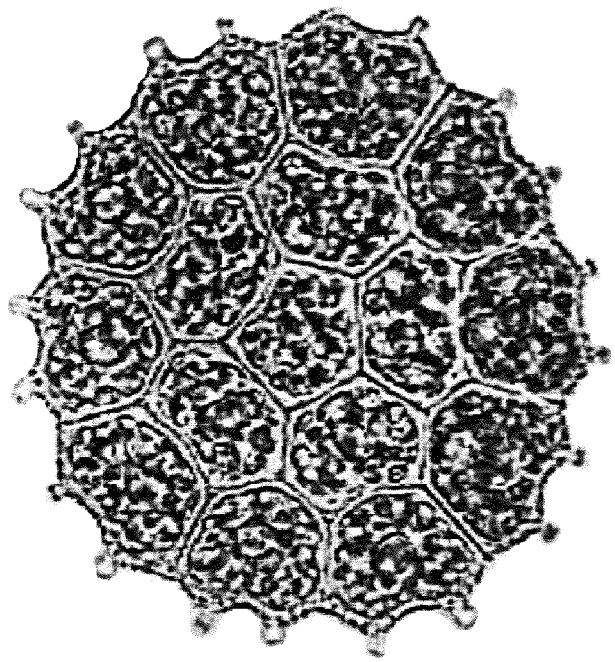
FIG. 6 is a picture of an example of a pediastrum algae.

Although any one or more of the algae species naturally found in waste water may be used, various embodiments of the present invention preferably use microalgae. Microalgae has a simple structure, a fast growth rate, and high oil content (for some species). An example of a diatom microalgae is the Pediastrum Duplex (see FIG. 6) which is in the Chlorophycease family. Commercial interests for large scale algal-cultivation systems could tie into existing infrastructures, such as sewage treatment facilities. This approach not only provides the raw materials for the system, such as $CO_2$ and nutrients; but it changes those wastes into resources.

Sewage treatment or domestic wastewater treatment facilities perform the process of removing contaminants from wastewater, both runoff (effluents) and domestic. It includes physical, chemical and biological processes to remove physical, chemical and biological contaminants. Its objective is to produce a waste stream (or treated effluent) and a solid waste or sludge suitable for discharge or reuse back into the environment. A system, according to one embodiment, uses the waste water effluent at multiple stages of treatment as nutrients for the production of diesel from algae using a semi-closed loop photobioreactor.

The sewage treatment involves three stages called primary, secondary, and tertiary treatment. First, the solids are separated from the wastewater stream. Then dissolved biological matter is progressively converted into a solid mass by using indigenous, water-borne microorganisms. Finally, the biological solids are neutralized then disposed of or re-used, and the treated water may be disinfected chemically or physically (for example by lagoons and micro-filtration). The final effluent can be discharged into a stream, river, bay, lagoon or wetland, or it can be used for the irrigation of a golf course, green way or park. If it is sufficiently clean, it can also be used for groundwater recharge.

Typical micro nutrients used in algae growth are: Ca, Cu, Fe, Mg, Mn, Mo, K, and Zn.

Algae reproduce by cellular division. They divide and divide until they fill the space they occupy and have consumed all of the nutrients in it. In the right environment, fresh algae cells grow and divide on a rapidly growing path, absorbing all available nutrients and light energy through photosynthesis. When the concentration of algae in the photobioreactor is high enough that light does not penetrate through the entire culture, the algae grows slower. This is called dark cycle photosynthesis. When the algae population fills the entire growth vessel and reaches a terminal density, it stops growing. As algae growth slows it generates more oil. The diesel photobioreactor optimizes growth cycles to induce oil production in the algae cells through controlling the algae photobioreactor environment creating optimum growth and no-growth states.

To capture the algae from the photobioreactor, algae is aggregated into larger more separable particles that allow for in-situ collection with continuous production. One method of aggregation is the exposure of algae to an ultrasonic wave.

There are three well-known methods to extract the oil from oilseeds, and these methods apply equally well for algae.

Expeller/Press is a mechanical method for extracting oil from raw materials. The raw materials are squeezed under high pressure in a single step. When used for the extraction of food oils and algae, which are supplied to the press in a continuous feed, expeller presses can recover 75% of the oil from algae. As the raw material is pressed, friction causes it to heat up.

Supercritical Fluid extraction can extract almost 100% of the oils all by itself. This method however needs special equipment for containment and pressure. In the supercritical fluid/CO2 extraction, CO2 is liquefied under pressure and heated to the point that it has the properties of both a liquid and gas. This liquefied fluid then acts as the solvent in extracting the oil.

Hexane Solvent Extraction can be used in isolation or it can be used along with the oil press/expeller method. After the oil has been extracted using an expeller, the remaining pulp can be mixed with cyclo-hexane to extract the remaining oil content. The oil dissolves in the cyclohexane, and the pulp is filtered out from the solution. The oil and cyclohexane are separated by means of distillation. These two stages (cold press & hexane solvent) together will be able to derive more than 95% of the total oil present in the algae.

Conventional mechanical methods are used to separate the oil, water and algae mass. The water is recycled back into the system, the oil is packaged for refining and distribution, and the algae mass is devoted to various "green" applications like animal feed, ethanol and construction materials.

After harvesting the algae, the diesel photobioreactor is flushed and cleaned in preparation for the next algae cycle.

Concentrated nutrients are created by subjecting the waste water to very high pressure prior to introducing the waste water to the photobioreactor. This process breaks the nutrients into smaller particles enabling increased surface area between the nutrients and the algae culture.

An integrated lighting system using light tubes supports a high efficiency algae production environment. The integrated lighting system, according to one embodiment, is deployed within the photobioreactor tube and is constructed of materials that greatly reduce or eliminate microalgae adhesion to the lighting system. The deployment of the lighting system within the photobioreactor eliminates the area on the photobioreactor tube that microalgae would naturally adhere to.

Transparent hollow light tubes, in contrast to an optical fiber which has a solid core, use a prism light guide that leads the light through air and is therefore referred to as hollow light guide. The light tubes are integrated into the sides of the photobioreactor tubes.

In one embodiment, a prism light guide is used in lighting for both transport and distribution of light. An optical lighting film can be used to create the light pipe providing a uniform distribution of the light over the entire length of the light pipe. A thin film incorporating microscopic prisms can be coupled with artificial light sources. An example of the thin film is the Light Tube™ from 3M. An example of artificial light sources is a sulfur lamp.

Sulfur plasma consists mainly of dimer molecules ($S_2$), which generate the light through molecular emission. The emission spectrum is continuous throughout the visible spectrum. The lamp's output is low in infrared energy, and less than 1% is ultraviolet light. As much as 73% of the emitted radiation is in the visible spectrum, far more than other types of lamps. The visible light output mimics sunlight better than any other artificial light source and lacks the harmful ultraviolet radiation. An example of a sulfur plasma light source is the Fusion Light Drive™ commercially available from Fusion Lighting.

The spectral output peaks at 510 nanometers, imparting a distinctly greenish hue to the illuminated environment. The correlated color temperature is approximately 6000 kelvins with a CRI of 79. The lamp can be dimmed to 15% without affecting the light quality, and light output remains constant over the life of the bulb.

Figure 1:
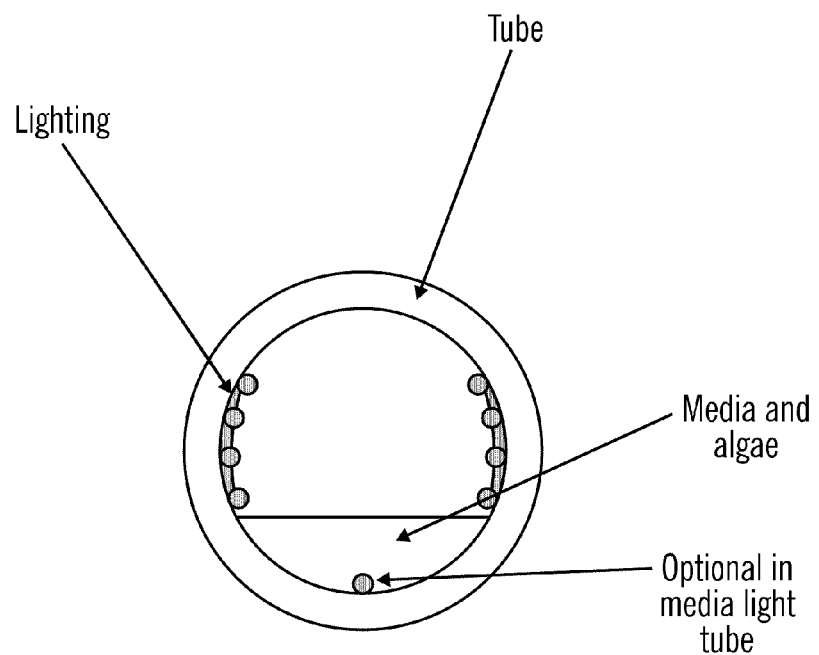
FIG. 1 is a cross section of an example of a photobioreactor tube, according to one embodiment of the present invention.
Figure 2:
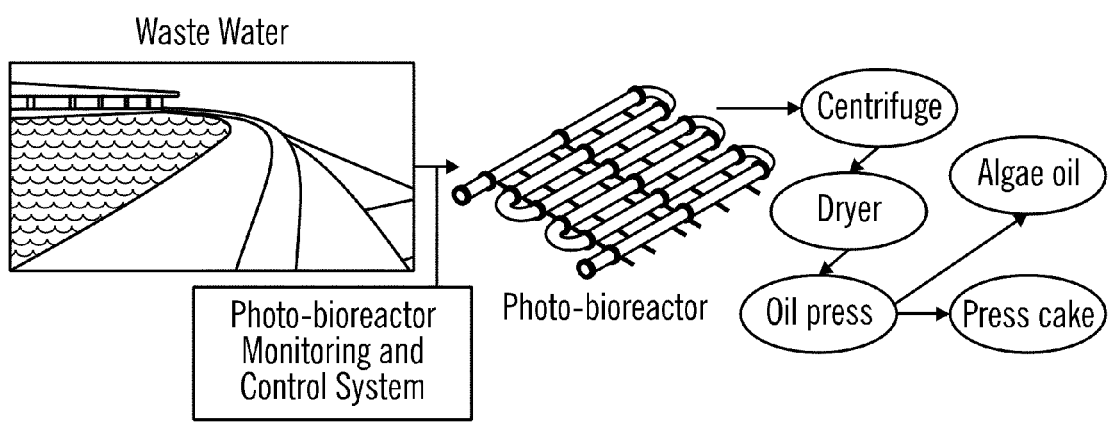
FIG. 2 is block diagram illustrating an example of a diesel fuel photobioreactor system according to one embodiment of the present invention.
Figure 3:
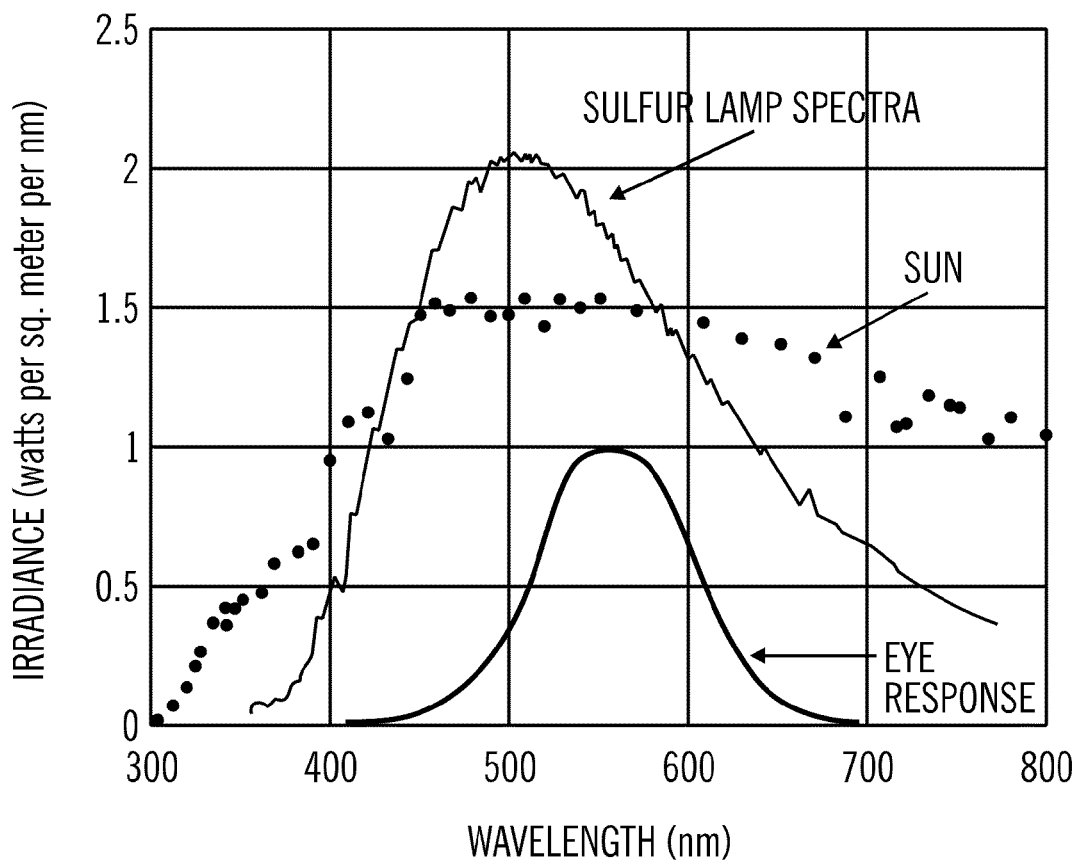
FIG. 3 is a graph illustrating sulfur lamp spectra.

The spectrum of the sulfur lamp is shown in FIG. 3. This figure also shows the spectrum of sunlight. It is obvious that the spectrum of the sulfur lamp corresponds quite closely with that of sunlight so that viewing under the sulfur lamp has practically the same appearance as viewing under sunlight conditions. The color temperature of the Fusion Light Drive™ 1000 watt lamp is about 6000° K.

As compared to the sunlight, the ultraviolet radiation is even lower, for wavelengths of <380 mm, it is only 0.14%. The same comment applies to the infrared radiation: for wavelengths >780 mm, it is less than 8%. These last two figures mean that when using this light source, a significantly lower level of ultraviolet radiation affecting the materials is exposed. This also means that algae growth under this lamp will be significantly greater when compared to other lighting technologies and even sunlight. It also may be estimated that the heat load will be more favorable as a result of the lower infrared content, as compared to sunlight.

Certain wavelengths can be damaging in terms of biomass yield. The light pipe can be tuned in a variety of methods such as using filters or dyes. The optimum wavelength will be defined for the specific algae species selected.

The (OLF): Optical Light Film from 3M causes light to be refracted in such a manner that when light hits the surface of the film at low angles it is totally reflected internally. The film can be formed into a cylinder (a light tube) with a sulfur light source at one end. The sulfur light source is optically coupled with the light tube. The light generated by the source will be contained within the cylinder (light tube). This is how the light pipe (or light tube) was developed. The outside of the light pipe radiates the light. None of the light needs to be lost if a mirror that reflects the light is installed at the opposite end of the cylinder. The cylinder will radiate the light with extremely good uniformity. The cylinder with its diameter of about 250 mm can be compared with a giant fluorescent tube. It is also possible to mask part of the light pipe (light tube) circumference with a reflective film. A construction of this nature, according to one embodiment, can be fitted into a photobioreactor tube with the light radiating into the photobioreactor tube in a very uniform manner.

Figure 4:
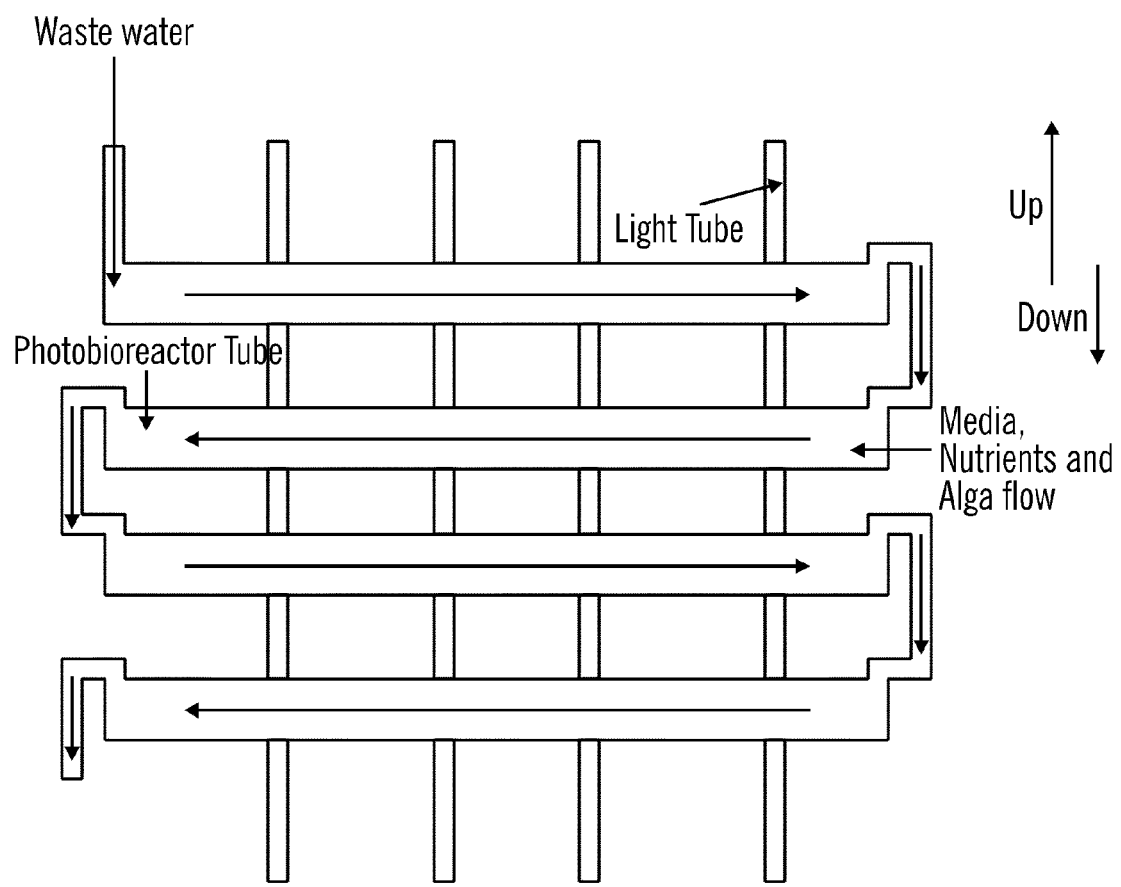
FIG. 4 shows an example of a vertical photobioreactor system, according to one embodiment of the present invention.

In another embodiment, such as illustrated in FIG. 4, one or more light tubes are integrated into a vertical flow system where the culture media and algae are inserted at the top of a vertical flow system. The light tubes are integrated into the vertical flow system to provide an even distribution of controlled lighting for the photobioreactor.

Figure 5:
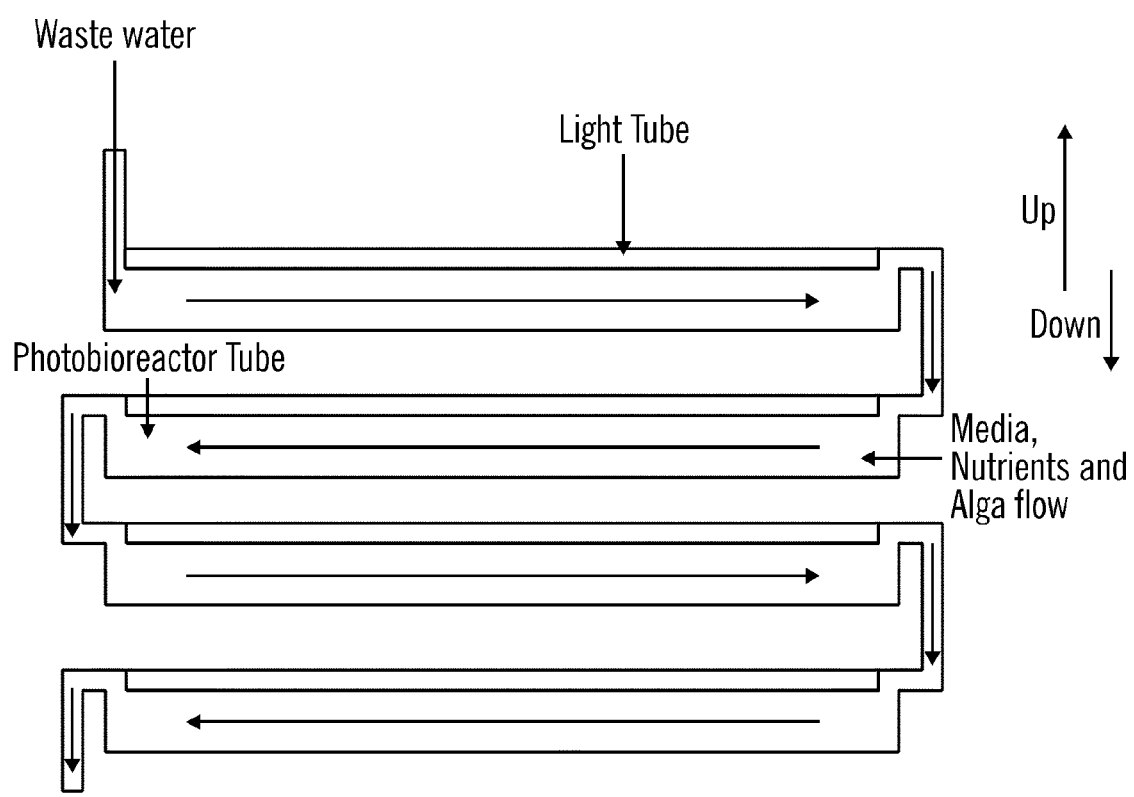
FIG. 5 shows an example of a vertical photobioreactor system with integrated light system, according to one embodiment of the present invention.
Figure 7:
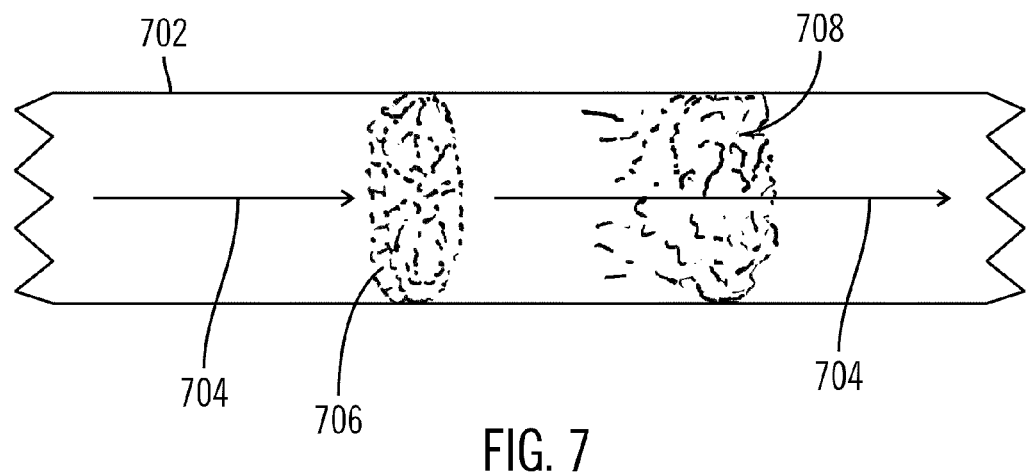
FIG. 7 is a side view of a photobioreactor tube, according to one embodiment of the present invention.
Figure 8:
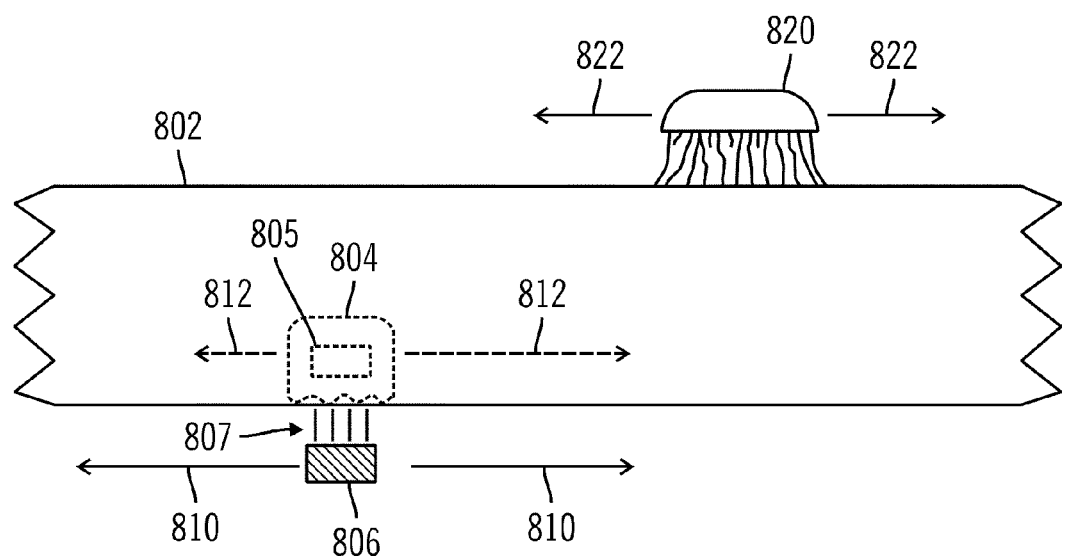
FIG. 8 is a side view of a photobioreactor tube, according to one embodiment of the present invention.

In another embodiment, such as illustrated in FIG. 5, one or more light tubes are placed adjacent to the photobioreactor tubes.

Biologists have categorized microalgae in a variety of classes, mainly distinguished by their pigmentation, life cycle and basic cellular structure. Microphytes are microscopic algae, typically found in freshwater and marine systems, and are often called microalgae.

Microalgae are unicellular species which exist individually, or in chains or groups. Depending on the species, their sizes can range from a few micrometers (μm) to a few hundreds of micrometers. In addition, because the cells grow in aqueous suspension, they have more efficient access to water, $CO_2$, and other nutrients.

Two important categories for the production of diesel oil are:

The diatoms (Bacillariophyceae). These algae dominate the phytoplankton of the oceans, but are also found in fresh and brackish water. Approximately 100,000 species are known to exist. Diatoms contain polymerized silica (Si) in their cell walls. All cells store carbon in a variety of forms. Diatoms store carbon in the form of natural oils or as a polymer of carbohydrates known as chyrsolaminarin.

The golden algae (Chrysophyceae) is a group of algae that is similar to the diatoms. They have more complex pigment systems, and can appear yellow, brown or orange in color. Approximately 1,000 species are known to exist primarily in freshwater systems. They are similar to diatoms in pigmentation and biochemical composition. The golden algae produce natural oils and carbohydrates as storage compounds.

It should be noted that besides diatoms, various types of algae such as the green algae may be used.

The coupling of the semi-closed loop algae photobioreactor using waste water as a nutrient for the generation of alga oil and the refinement to diesel and other byproducts with a waste water treatment facility offers substantial economic benefits.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A diesel photobioreactor system, comprising:
a semi-closed loop container that draws waste water to supply nutrients and create a culture medium for photosynthetic organisms to a photobioreactor constructed from materials that efficiently allow light into the container for cultivating photosynthetic organisms wherein the container comprises a light tube used to distribute controlled light across the photobioreactor tube.

2. The diesel photobioreactor system of claim 1, wherein the container is constructed as a vertical flow device where the culture medium and algae are inserted in the top of a continuous flow tube and move horizontally to one or more ports that allow the culture medium and algae to flow down to a next level, and this process is repeated until it reaches a bottom tube where the culture medium and algae are pumped back to the top of the vertical flow device or passed to outside of the vertical flow device to a next process.

3. The diesel photobioreactor system of claim 1, wherein the container comprises a photobioreactor tube, and the system further comprising a set of cleaning brushes that are movably located in the container and are moved by water pressure through the container to clean the inner surface of the photobioreactor tube.

4. The diesel photobioreactor system of claim 1, further comprising a cleaning device that is moved through the photobioreactor tube by water propulsion through the tube, cleaning the inner sides of the tube as the cleaning device passes through the tube.

5. The diesel photobioreactor system of claim 4, wherein the cleaning device comprises a cleaning solvent or microbes that are used to clean the inner surface of the photobioreactor tube.

6. The diesel photobioreactor system of claim 1, further comprising a cleaning device that is moved through the photobioreactor tube by magnetic propulsion, wherein a magnet is located in the cleaning device deployed inside the tube, and the cleaning device with the magnet is drawn through the tube by a second magnet passing along the outside of the tube, thereby cleaning the inner side of the tube as the cleaning device passes through the tube.

7. The diesel photobioreactor system of claim 1, further comprising a cleaning device deployed outside of the photobioreactor tube, the cleaning device using clean water and brushing to clean the outer surface of the photobioreactor tube.

8. The diesel photobioreactor system of claim 1, wherein carbon-dioxide is provided in the photobioreactor tube to stimulate algae growth.

9. The diesel photobioreactor system of claim 1, wherein the system comprises a closed loop system to protect the selected algae species from being contaminated by other algae species and bacteria and to control optimum waste water temperature, PH, carbon-dioxide concentration, gas composition, and irradiance.

10. The diesel photobioreactor system of claim 1, wherein the system is monitored on a real-time basis for contamination by other algae species and bacteria, waste water temperature, PH, carbon-dioxide concentration, gas composition, and irradiance.

11. The diesel photobioreactor system of claim 1, wherein the system is regulated on a real-time basis for waste water temperature, PH, carbon-dioxide concentration, conductivity, light, gas composition, and irradiance.

12. The diesel photobioreactor system of claim 1, wherein the waste water is subjected to high pressure prior to being introduced to the photobioreactor system.

13. The diesel photobioreactor system of claim 1, further comprising a sulfur light source lamp, optically coupled with the light tube, and used as a light source for the light tube.

14. The diesel photobioreactor system of claim 1, wherein natural sunlight or moonlight is used as a light source for the light tube.

15. The diesel photobioreactor system of claim 1, wherein concentrated sunlight or moonlight is used as a light source for the light tube.

16. The diesel photobioreactor system of claim 1, wherein the light tube is placed in close proximity to the photobioreacture tube.

17. The diesel photobioreactor system of claim 1, wherein the light spectrum is adjusted for optimum algae growth.

18. A method for cultivating photosynthetic organisms that are used to produce diesel fuel, the method comprising:
- inserting photosynthetic algae organisms and culture medium in a first photobioreactor tube;
- moving the algae and culture medium horizontally through the first photobioreactor tube;
- moving the algae and culture medium through a port out of the first photobioreactor tube and flowing through another port into a second photobioreactor tube at a lower level;
- moving the algae and culture medium horizontally through the second photobioreactor tube; and
- irradiating light into the first and second photobioreactor tubes for cultivating the photosynthetic algae organisms that are used to produce diesel fuel, and where a light tube is used to distribute controlled light across the first and second photobioreactor tubes.

19. The method of claim 18, further comprising:
- pumping the algae and culture medium back up to the first photobioreactor tube to repeat a cultivation process for cultivating the photosynthetic algae organisms.

\* \* \* \* \*